United States Patent [19]
Leaverton et al.

[11] Patent Number: 5,665,228
[45] Date of Patent: Sep. 9, 1997

[54] OZONE MIXING SYSTEM FOR A HYDROTHERAPY SPA

[75] Inventors: Gregg W. Leaverton; Steven A. Rork; Edward G. Ramsauer, all of Oceanside, Calif.

[73] Assignee: Dimension One Spas, Inc., Oceanside, Calif.

[21] Appl. No.: 730,145

[22] Filed: Oct. 15, 1996

Related U.S. Application Data

[63] Continuation of Ser. No. 589,400, Jan. 22, 1996.

[51] Int. Cl.$^6$ .................................................. C02F 1/78
[52] U.S. Cl. ...................... 210/169; 210/188; 210/192; 210/195.1; 210/760
[58] Field of Search .................................. 210/760, 169, 210/188, 192, 195.1, 752, 765, 194

[56] References Cited

U.S. PATENT DOCUMENTS

| | | | |
|---|---|---|---|
| 4,053,403 | 10/1977 | Bachhofer et al. | 210/760 |
| 4,098,691 | 7/1978 | Filby | 210/760 |
| 4,353,717 | 10/1982 | Herbrechtsmeier | 210/760 |
| 4,752,401 | 6/1988 | Bodenstein | 210/760 |
| 4,959,142 | 9/1990 | Dempo | 210/167 |
| 4,995,123 | 2/1991 | Kern | 210/760 |
| 5,032,292 | 7/1991 | Conrad | 210/760 |
| 5,075,016 | 12/1991 | Barnes | 210/760 |
| 5,116,574 | 5/1992 | Pearson | 210/760 |
| 5,173,257 | 12/1992 | Pearson | 210/760 |
| 5,174,905 | 12/1992 | Shaw | 210/760 |
| 5,178,755 | 1/1993 | La Crosse | 210/760 |
| 5,256,307 | 10/1993 | Bachhofer et al. | 210/760 |
| 5,376,265 | 12/1994 | Szabo | 210/188 |
| 5,397,480 | 3/1995 | Dickerson | 210/760 |
| 5,427,693 | 6/1995 | Mausgrover et al. | 210/760 |

*Primary Examiner*—Cynthia L. Nessler
*Attorney, Agent, or Firm*—Rodney F. Brown

[57] ABSTRACT

A mixing system for introducing ozone into water of a hydrotherapy spa includes filter for filtering water from said hydrotherapy spa. A pump draws water from said hydrotherapy spa through said filter. A first injector includes a first input for receiving filtered water from said filter, a second input for receiving ozone, and an output for providing a first mixture of ozone in solution with said filtered water and ozone not in solution with said filtered water. A recapturing unit, coupled to said output of said first injector, separates said ozone not in solution with said filtered water from said first mixture. A second injector, having a first input coupled to said recapturing unit, a second input coupled to said filter, and an output, provides a second mixture of said ozone not in solution with said filtered water and said filtered water at said output of said second injector means.

18 Claims, 4 Drawing Sheets

OZONE MIXING SYSTEM FOR A HYDROTHERAPY SPA

This is a continuation of U.S. patent application Ser. No. 08/589,400, filed on Jan. 22, 1996.

TECHNICAL FIELD

This invention relates to hydrotherapy spas, and more particularly, to an ozone mixing system for a hydrotherapy spa.

BACKGROUND OF THE INVENTION

Hydrotherapy spas typically include a filtration system with a filter, a circulation pump and a heater for cleaning and heating the spa water. Because the water in the hydrotherapy spa is typically heated above 90° F., bacteria grows in the water and presents a health hazard to users of the hydrotherapy spa. Preferably, the hydrotherapy spa includes a water treatment system to prevent the growth of such bacteria.

Conventional hydrotherapy spas use ozone mixing systems for introducing ozone into the water. The ozone mixing systems are typically associated with the filtration system. Ozone in solution with the spa water eliminates bacteria in the water and thereby reduces possible health hazards associated with the bacteria.

Conventional ozone mixing systems, however, do not effectively mix the ozone with the water. The ozone which is not properly mixed with the water escapes in the atmosphere. If the hydrotherapy spa is located indoors, the ozone can build up to undesirable levels and adversely impact air quality. Likewise, the ozone escaping into the atmosphere does not treat the water and eliminate bacteria.

Referring to FIG. 1, a prior art ozone mixing system 10 for a hydrotherapy spa 12 is illustrated. A circulation pump 14 draws water 18 from the hydrotherapy spa 12 through a filter 22 having an input located below water line 24. Circulation pump 14 pumps water through a heater 26 to a first input of an injector 30.

An ozone generator 34 converts air from a supply 38 into ozone, the ozone is output to a second input of an ozone injector 30. Ozone injector 30 creates a first mixture including ozone in solution with filtered water and ozone not in solution with filtered water. The first mixture is conveyed via conduit 42 back into the hydrotherapy spa 12.

As can be appreciated, the ozone which is not in solution with the filtered water escapes into the atmosphere 50 without providing beneficial water treatment effects such as eliminating bacteria. Furthermore, the ozone entering the atmosphere adversely impact air quality, particularly if the hydrotherapy spa 14 is located indoors.

Therefore, an ozone mixing system which increase the amount of ozone mixed in solution with spa water to increase the elimination of bacteria and which reduces the amount of ozone entering the atmosphere is desirable.

SUMMARY OF THE INVENTION

A mixing system for introducing ozone into water of a hydrotherapy spa according to the present invention includes filter means for filtering water from said hydrotherapy spa. A pump means draws water from said hydrotherapy spa through said filter means. A first injector means includes a first input for receiving filtered water from said filter means, a second input for receiving ozone, and an output for providing a first mixture of ozone in solution with said filtered water and ozone not in solution with said filtered water. A recapturing means, coupled to said output of said first injector means, separates said ozone not in solution with said filtered water from said first mixture. A second injector means, having a first input coupled to said recapturing means, a second input coupled to said filter means, and an output, provides a second mixture of said ozone not in solution with said filtered water and said filtered water at said output of said second injector means.

According to one feature of the invention, the output of said second injector means is coupled to said hydrotherapy spa and the recapturing means outputs said ozone in solution with said filtered water to said hydrotherapy spa.

According to one feature of the invention, the ozone mixing system further includes an "L"-shaped conduit for connecting said output of said first injector means to an output of said recapturing means.

According to one feature of the invention, the recapturing means includes an outer vertical conduit and an inner vertical conduit located inside said outer vertical conduit.

According to one feature of the invention, an upper portion of said inner vertical conduit is coupled to said output of said first injector means.

According to one feature of the invention, the inner vertical conduit has a length shorter than a length of said outer vertical conduit.

According to one feature of the invention, said first input of said second injector means is coupled to an upper portion of said outer vertical conduit.

According to one feature of the invention, an outer vertical conduit and said inner vertical conduit are cylindrical.

According to one feature of the invention, the ozone mixing system further includes a return conduit, coupled to said outer vertical conduit and said hydrotherapy spa, for delivering said ozone in solution with said filtered water to said hydrotherapy spa.

According to one feature of the invention, the ozone mixing system further includes heating means for heating filtered water output by said filter means.

According to one feature of the invention, the ozone mixing system further includes a "T"-shaped connector, coupled to an output of said pump means, for providing filtered water to said first input of said first injector means and to said second input of said second injector means.

In another aspect of the present invention, an ozone recapturing device, coupled to ozone mixing means for mixing ozone and water, improves the amount of ozone in solution with water in a hydrotherapy spa. The ozone recapturing device includes an input for receiving from said first mixing means a first mixture including ozone in solution with water and ozone not in solution with water. An inner vertical conduit has an upper portion coupled to said input. An outer vertical conduit is mounted outside said inner vertical conduit and has a length longer than a length of said inner vertical conduit. A connecting means for connecting an upper portion of said inner and outer vertical conduits together. The ozone not in solution with said filtered water collects between said upper portion of said inner and outer vertical conduits. A first output is located on a lower portion of said outer vertical conduit. A second output coupled to said upper portion of said outer vertical conduit.

Other objects, features and advantages will be readily apparent.

BRIEF DESCRIPTION OF THE DRAWINGS

The various advantages of the present invention will become apparent to those skilled in the art after studying the following specification and by reference to the drawings in which.

DESCRIPTION OF THE PREFERRED EMBODIMENT

Figure 1:
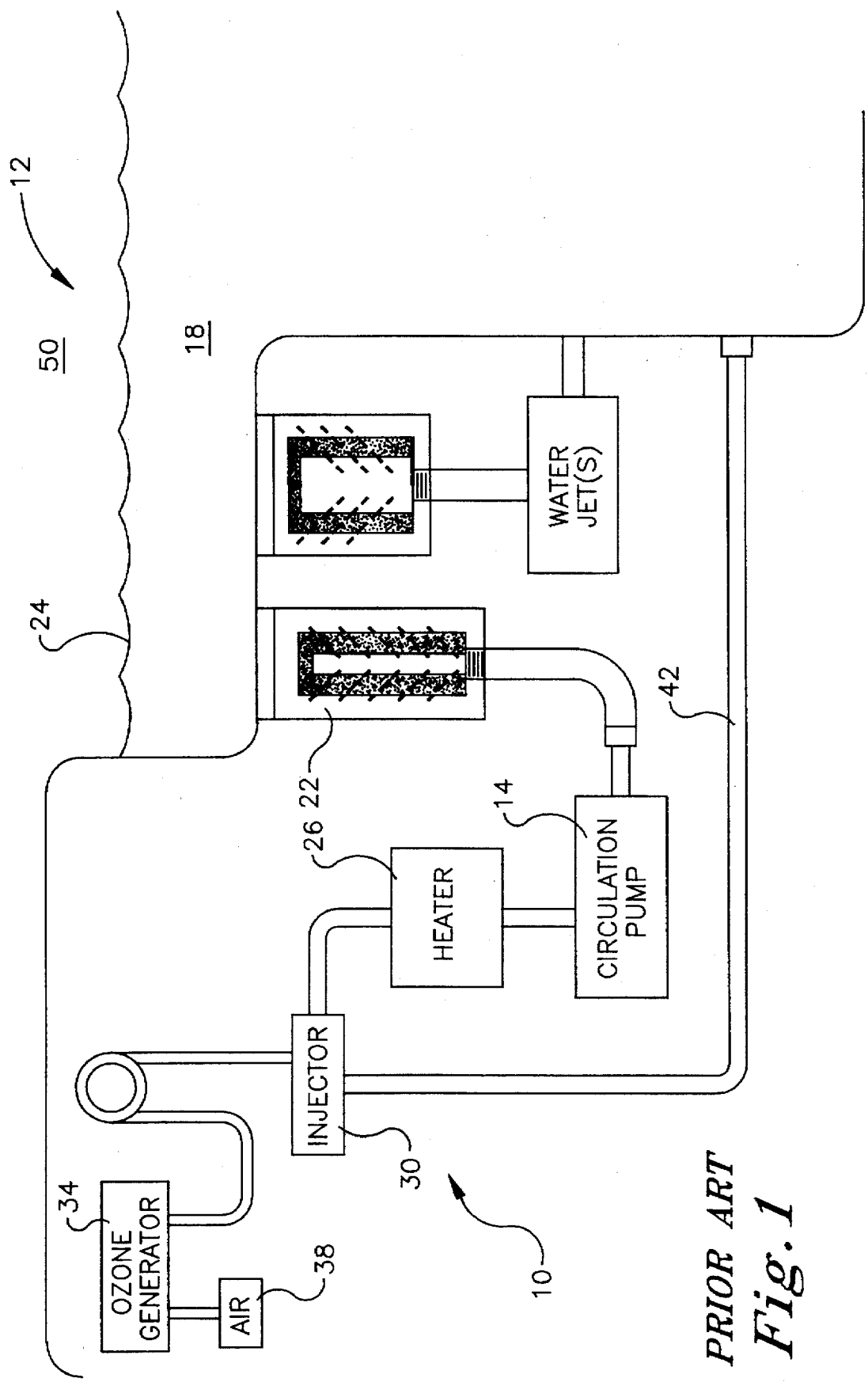
FIG. 1 illustrates a hydrotherapy spa including an ozone mixing system according the prior art.
Figure 2:
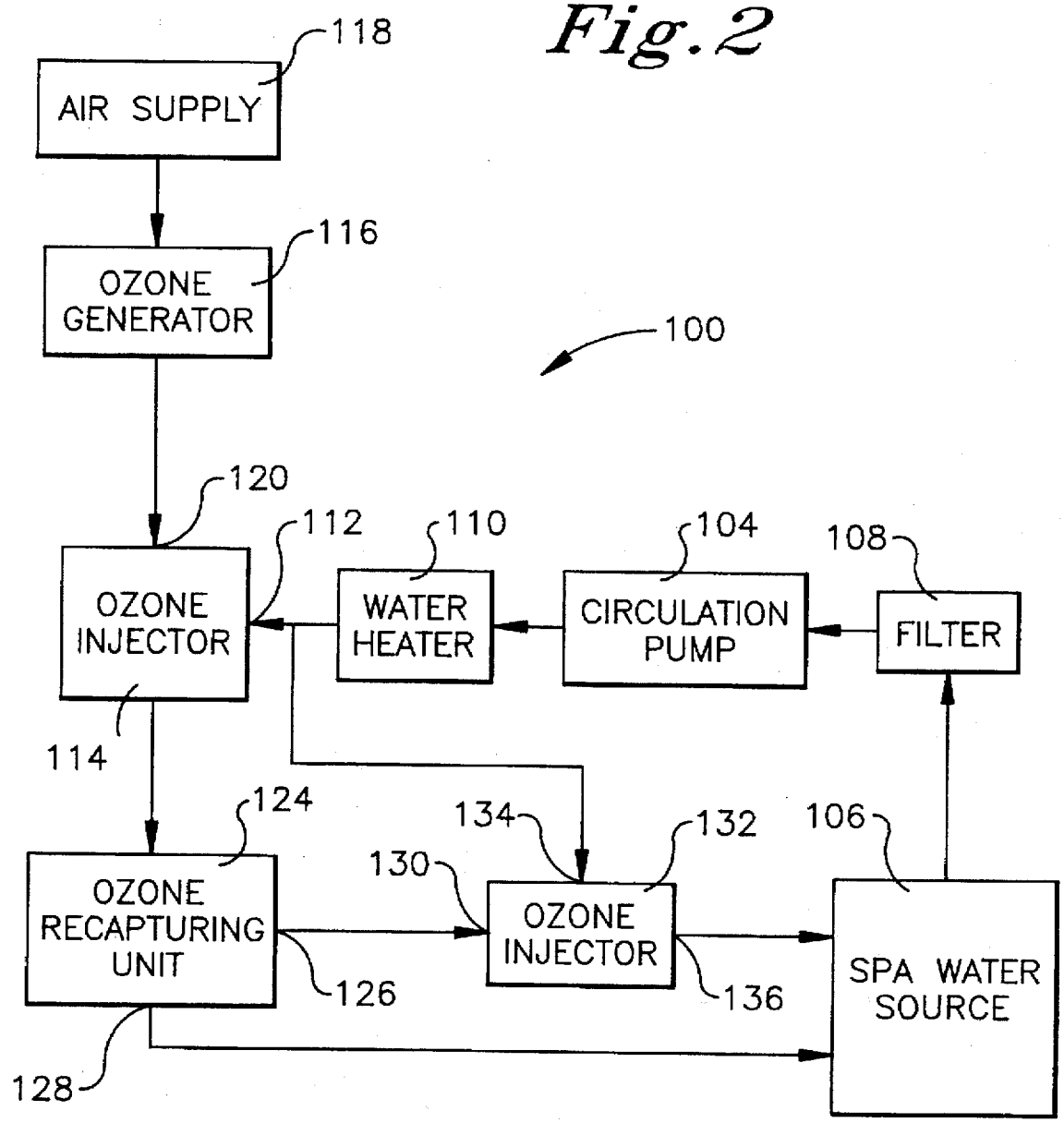
FIG. 2 is a block diagram of an ozone mixing system according to the present invention.

Referring to FIG. 2, the presently preferred ozone mixing system 100 according to the present invention is illustrated in block diagram form. Ozone mixing system 100 includes a circulation pump 104 which draws spa water from a spa water source 106, such as a hydrotherapy spa, through a filter 108. Circulation pump 104 pumps filtered water through a heater 110 and into a first input 112 of ozone injector 114.

An ozone generator 116 converts air from a supply 118 into ozone which is output to a second input 120 of ozone injector 114. Ozone injector 114 mixes the ozone with the filtered water. Some of the ozone, however, is not fully absorbed by the water. Therefore, ozone injector 114 outputs a first mixture including ozone in solution with the filtered water and ozone not in solution with the filtered water. The ozone not in solution with the filtered water is typically in the form of bubbles. As can be appreciated, the outer surface of the ozone bubbles is in contact with the water and coacts therewith. The ozone in direct contact with the water can go into solution with the water. In contrast, ozone not in direct contact with water cannot go into solution. As will be described below, the present invention includes several right angle conduits which break the ozone bubbles into smaller ozone bubbles thereby increasing the surface area of ozone in contact with the water.

An output of ozone injector 114 is coupled to an ozone recapturing unit 124 which separates the ozone not in solution with the filtered water from the first mixture and outputs the ozone not in solution with the filtered water at a first output 126 thereof. Ozone recapturing unit 124 outputs ozone in solution with the filtered water at a second output 128 thereof.

First output 126 of ozone recapturing unit 124 is coupled to a first input 130 of a second ozone injector 132. A second input 134 of ozone injector 132 is coupled to filtered water from heater 110. Second ozone injector 132 injects the ozone not in solution with filtered water from ozone recapturing unit 124 into the filtered water from heater 110 to provide increase the ozone mixing. An output 136 of ozone injector 132 is coupled to spa water source 106.

Figure 3:
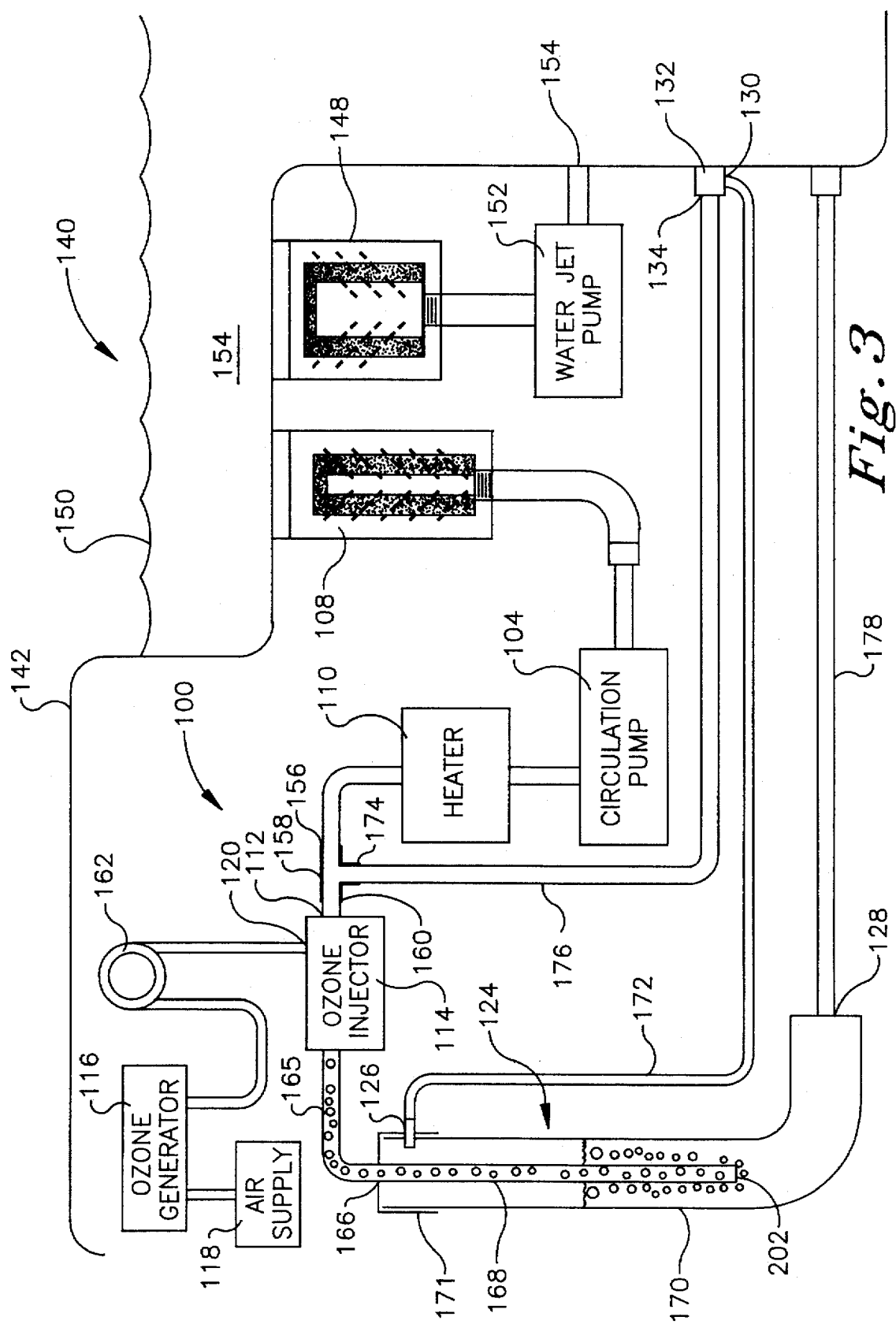
FIG. 3 is a more detailed illustration and partial block diagram of a hydrotherapy spa including the ozone mixing system according to the present invention and illustrated in FIG. 2.

For purposes of clarity, reference numerals from FIG. 2 are employed in FIG. 3 where appropriate. FIG. 3 illustrates a hydrotherapy spa 140 including the ozone mixing system 100 and a spa shell 142. Filter 108 and a second filter 148 are positioned below a water line 150 in use. A water jet pump 152 which does not form part of the ozone mixing system 100 draws water 154 through second filter 148 and propels the filtered water through one or more nozzles 154 formed in spa shell 142 in a conventional manner.

Circulation pump 104 draws water 154 through first filter 108 and pumps the filtered water through heater 110 to a first input 156 of a "T"-shaped conduit 158. A first output 160 of "T"-shaped conduit is coupled to first input 112 of ozone injector 114. Ozone generator 116 which is coupled to air supply 118 generates ozone which is output via conduit 162 to second input 120 of ozone injector 114. An output 164 of ozone injector 114 is coupled via a "L"-shaped conduit 165 to an input 166 of ozone recapturing unit 124.

Ozone recapturing unit 124 includes an inner vertical conduit 168 which is housed inside of an outer vertical conduit 170. An end cap connector 171 joins the inner and outer conduits 168 and 170. Inner conduit 168 has a vertical length shorter than outer conduit 170. In a highly preferred embodiment, the outer conduit is approximately 6" longer than the inner conduit. A conduit 172, coupled to a first output 126 of ozone recapturing unit 124, conveys ozone collected by recapturing unit 124 to first input 130 of second ozone injector 132. A conduit 176 connects a second output 174 of "T"-shaped conduit 158 to second input 134 of second ozone injector 132.

Output 128 of ozone recapturing unit 128 is coupled via conduit 178 to spa shell 142 and conveys ozone in solution with filtered water to hydrotherapy spa 140.

Figure 4:
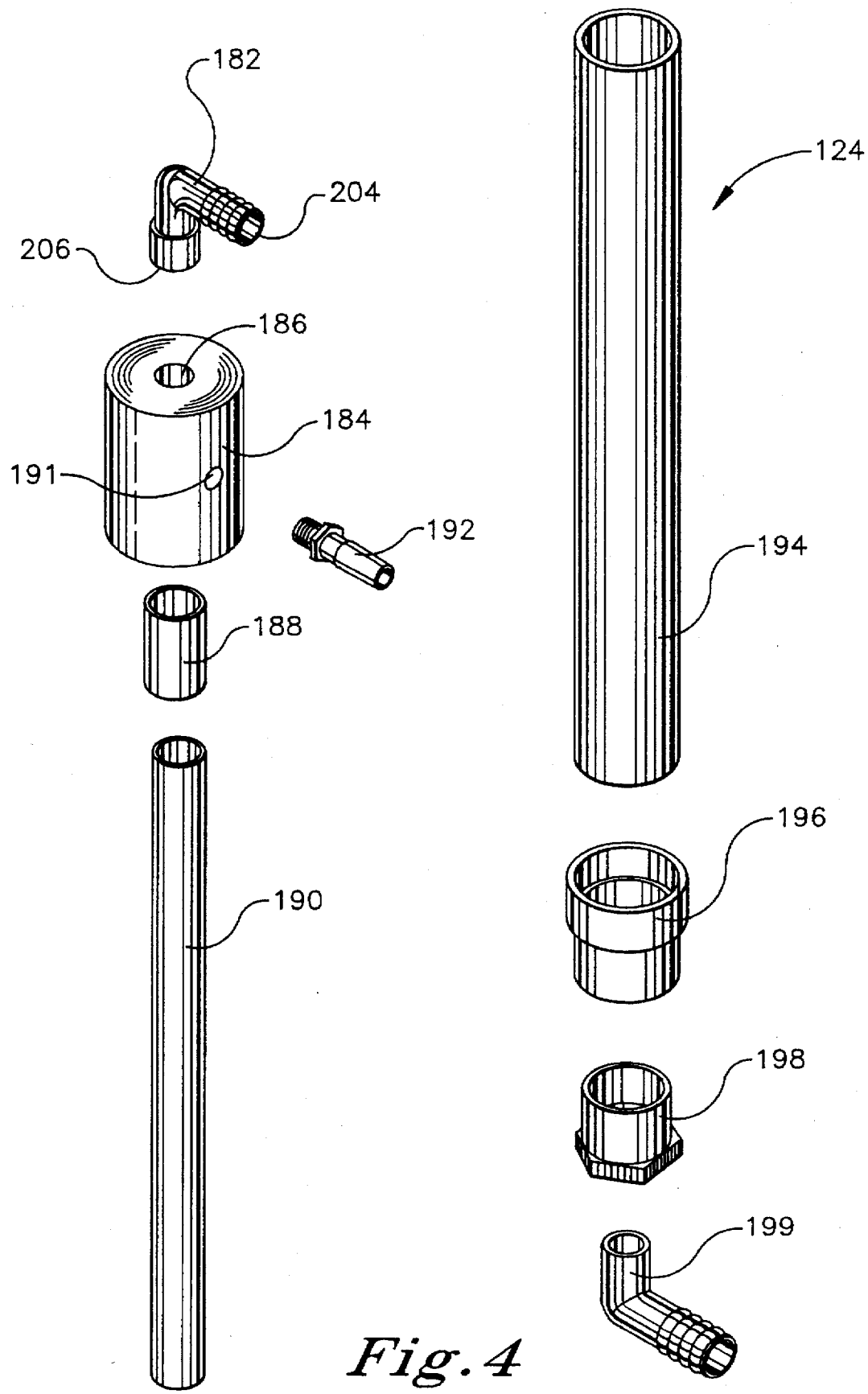
FIG. 4 illustrates an assembly view of an ozone recapturing device according to the present invention.

In FIG. 4, an assembly view of a preferred embodiment of ozone recapturing unit 124 is illustrated. An "L"-shaped connector 182 couples an output of first ozone injector 114 to a cylindrical end cap 184. Cylindrical end cap 184 includes a bore 186 for receiving "L"-shaped connector 182. "L"-shaped connector 182 extends downwardly and is matingly received in one end of a cylindrical connector 188. An opposite end of cylindrical connector 188, in turn, matingly receives one end of an elongate conduit 190. Cylindrical end cap 184 further includes a second bore 191 for receiving a connector 192 which is coupled to conduit 172 in use.

A second elongate conduit 194 is coupled to one end of a transition connector 196. An opposite of transition connector 196 is coupled to one end of an end cap 198. One end of "L"-shaped connector 199 is received in an opposite end of end cap 198. An opposite end of "L"-shaped connector 199 is coupled to conduit 178.

In use, circulation pump 104 draws water through filter 108. Circulation pump 104 pumps the filtered water through heater 110 and into first input 156 of "T"-shaped conduit 158. "T"-shaped conduit outputs the filtered water via first and second outputs 160 and 174.

First output 160 is coupled to first input 112 of ozone injector 114. Ozone generator 116 outputs ozone to second input 120 of ozone injector 114. Ozone injector 114 mixes ozone with the filtered water. Some of the ozone is not fully mixed with the filtered water and forms bubbles in the filtered water. Thus, ozone injector 114 generates a first mixture of ozone in solution with the filtered water and ozone not in solution with the filtered water.

The first mixture is output via "L"-shaped conduit 165 to the ozone recapturing unit 124. Advantageously, ozone bubbles are broken apart when traversing the corner of the "L" shaped conduit 165. As a result, the surface area of ozone in contact with and able to coact with the water increases.

The first mixture travels downwardly through inner vertical conduit 168. Upon reaching a lower opening 202 of inner vertical conduit 168, the ozone not in solution with the filtered water (e.g. ozone bubbles) moves in an upward direction and is captured in an upper portion of outer vertical conduit 170. Advantageously, the ozone bubbles are also broken up when traveling around the opening 202 and rising to the upper portion of the outer conduit 170. The ozone in solution with the filtered water, on the other hand, is output via conduit 178 into a hydrotherapy spa 140. The ozone in solution with the filtered water eliminates bacteria in the water.

The ozone not in solution with the filtered water collects in the upper portion of outer vertical conduit 170, exits output 126, traverses conduit 172, and enters first input 130 of second ozone injector 132. As previously mentioned, the second output 174 of "T"-shaped conduit 158 provides filtered water to second input 134 of second ozone injector 132. Advantageously, the ozone not in solution with the filter water after mixing by the first ozone injector 114 is recaptured by the recapturing unit 124 and mixed again with filtered water. This second mixing increases the amount of ozone in solution with the filtered water and, consequently, the elimination of undesirable bacteria in the spa water 154.

Referring to FIG. 4, the first mixture enters a first input 204 of "L"-shaped connector 182 and exits an output 206 thereof. Cylindrical connector 188 and elongate conduit 190 direct the first mixture downwardly. The ozone in solution with the filtered water from the first mixture collects in the lower portion of second elongate conduit 194, transition 196 and end cap 198 and is output via "L"-shaped connector 199 and conduit 178 to the hydrotherapy spa.

The ozone not in solution with the filtered water bubbles in an upwardly direction to an upper portion of elongate outer conduit 194 and cylindrical end cap 184 and is output via bore 191 and connector 192 to conduit 172 for subsequent mixing with filtered water at second ozone injector 132.

As can be appreciated from the foregoing, the ozone mixing system according to the present invention mixes ozone with spa water in a far mor efficient manner than previously accomplished. As a result, the amount of ozone escaping into the atmosphere is decreased and possible health hazards associated with such release of ozone into the atmosphere is highly reduced or even eliminated. In addition, concentrations of ozone in the spa water is increased to enhance the elimination of bacteria in the water.

In a highly preferred embodiment, conduit 162 is preferably a double Hartford loop having a 3/16" inner diameter. Preferably ozone injector 114 is a Mazzei injector made in accordance with U.S. Pat. No. 4,123,800 issued to Angelo L. Mazzei, hereby incorporated by reference. Preferably air supply 118 provides an air flow greater than one cubic foot per hour. Preferably ozone generator 116 generates ozone at a temperature less than 130° F. Preferably conduit 165 is approximately 10' long.

Various other advantages of the present invention will become apparent to those skilled in the art after having the benefit of studying the foregoing text and drawings, take in conjunction with the following claims.

We claim:

1. A mixing system for ozonating water of a hydrotherapy spa, said mixing system comprising:
   a reservoir containing a water to be ozonated;
   means for splitting said water to be ozonated into a first portion and a second portion;
   means for contacting said first portion of said water to be ozonated with a fresh ozone stream to form a first solution of water and ozone, wherein said first portion contacting means includes a first input for receiving said first portion of said water to be ozonated from said splitting means, a second input for receiving said fresh ozone stream, and an output for discharging a first mixture containing said first solution of water and ozone and an undissolved ozone stream;
   means coupled to said output of said first injector means for recapturing undissolved ozone by separating said undissolved ozone stream from said first solution of water and ozone; and
   means for contacting said second portion of said water to be ozonated with said undissolved ozone stream to form a second solution of water and ozone, wherein said second portion contacting means has a first input coupled to said recapturing means for receiving said undissolved ozone stream, a second input coupled to said splitting means for receiving said second portion of said water to be ozonated, and an output for discharging said second solution of water and ozone into said reservoir.

2. The mixing system of claim 1 wherein said output of said second portion contacting means is coupled to said reservoir and wherein said recapturing means outputs said first solution of water and ozone to said reservoir.

3. The mixing system of claim 1 further comprising means for heating said water to be ozonated.

4. The mixing system of claim 1 further comprising an "L"-shaped conduit for connecting said output of said first portion contacting means to an input of said recapturing means.

5. The mixing system of claim 1 wherein said recapturing means comprises an outer vertical conduit and an inner vertical conduit located inside said outer vertical conduit.

6. The mixing system of claim 5 wherein an upper portion of said inner vertical conduit is coupled to said output of said first portion contacting means.

7. The mixing system of claim 5 wherein said inner vertical conduit has a length shorter than a length of said outer vertical conduit.

8. The mixing system of claim 5 wherein said first input of said second portion contacting means is coupled to an upper portion of said outer vertical conduit.

9. The mixing system of claim 5 wherein said outer vertical conduit and said inner vertical conduit are cylindrical.

10. The mixing system of claim 5 wherein an upper portion of said inner vertical conduit is coupled to said output of said first portion contacting means, and further wherein said inner vertical conduit has a length shorter than a length of said outer vertical conduit.

11. The mixing system of claim 5 wherein said first input of said second portion contacting means is coupled to an upper portion of said outer vertical conduit, and further-wherein said outer vertical conduit and said inner vertical conduit are cylindrical.

12. The mixing system of claim 5 further comprising a return conduit coupled to said outer vertical conduit and said reservoir for discharging said first solution of water and ozone to said reservoir.

13. The mixing system of claim 1 further comprising means for drawing said water to be ozonated from said reservoir.

14. The mixing system of claim 13 wherein said splitting means is a T-shaped connector coupled to an output of said drawing means for providing said first portion of said water to be ozonated to said first input of said first portion contacting means and for providing said second portion of said water to be ozonated to said second input of said second portion contacting means.

15. A mixing system for ozonating water of a hydrotherapy spa, said mixing system comprising:

a reservoir containing a water to be ozonated;

a reservoir outlet line in fluid communication with said reservoir for withdrawing said water to be ozonated from said reservoir;

an ozone source having an ozone source outlet line;

a split in said reservoir outlet line, said split providing a first ozone injector inlet line for a first portion of said water to be ozonated and a second ozone injector line for a second portion of said water to be ozonated;

a first ozone injector having a first ozone injector outlet line and receiving said first ozone injector inlet line and said ozone source outlet line, wherein said first ozone injector contacts said first portion of said water to be ozonated from said first ozone injector inlet line with a fresh ozone stream from said ozone source outlet line to form a first solution of water and ozone and discharges a first mixture containing said first solution of water and ozone and an undissolved ozone stream via said first ozone injector outlet line;

a recapturing unit having a recaptured ozone outlet line and receiving said first ozone injector outlet line, wherein said recapturing unit separates said undissolved ozone stream and said first solution of water and ozone from said first ozone injector inlet line; and a second ozone injector having a second ozone injector outlet line and receiving said recaptured ozone outlet line and said second ozone injector inlet line, wherein said second ozone injector contacts said second portion of said water to be ozonated from said second ozone injector inlet line with said undissolved ozone stream from said recaptured ozone outlet line to form a second solution of water and ozone.

16. The mixing system of claim 15 further comprising a pump for displacing said water to be ozonated through said reservoir outlet line.

17. The mixing system of claim 15 wherein said second ozone injector outlet line is in fluid communication with said reservoir to discharge said second solution of water and ozone into said reservoir.

18. The mixing system of claim 15 wherein said recapturing unit has a first solution outlet line in fluid communication with said reservoir to discharge said first solution of water and ozone into said reservoir.

* * * * *

UNITED STATES PATENT AND TRADEMARK OFFICE
CERTIFICATE OF CORRECTION

PATENT NO. : 5,665,228
DATED : September 9, 1997
INVENTOR(S) : Gregg W. Leaverton, et. al.

It is certified that error appears in the above-identified patent and that said Letters Patent is hereby corrected as shown below:

Column 7, line 23: delete "cutlet" and insert --outlet--.

(Page 11, line 17)

Signed and Sealed this

Thirteenth Day of January, 1998

Attest:

BRUCE LEHMAN

Attesting Officer

Commissioner of Patents and Trademarks